United States Patent
Düppuis

(10) Patent No.: US 10,617,464 B2
(45) Date of Patent: Apr. 14, 2020

(54) INSTRUMENT FOR VESSEL FUSION AND SEPARATION

(71) Applicant: Erbe Elektromedizin GmbH, Tuebingen (DE)

(72) Inventor: Martina Düppuis, Pliezhausen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 68 days.

(21) Appl. No.: 14/208,792

(22) Filed: Mar. 13, 2014

(65) Prior Publication Data
US 2014/0276806 A1    Sep. 18, 2014

(30) Foreign Application Priority Data

Mar. 15, 2013 (EP) .................................... 13159361

(51) Int. Cl.
*A61B 18/14* (2006.01)
*A61B 18/00* (2006.01)

(52) U.S. Cl.
CPC .. *A61B 18/1445* (2013.01); *A61B 2018/0063* (2013.01); *A61B 2018/1455* (2013.01)

(58) Field of Classification Search
CPC .... A61B 2018/0063; A61B 2018/1455; A61B 18/085; A61B 18/1442; A61B 18/1445
See application file for complete search history.

(56) References Cited

U.S. PATENT DOCUMENTS

| 5,462,546 A | * | 10/1995 | Rydell | A61B 18/1445 606/48 |
| 5,766,167 A | * | 6/1998 | Eggers | A61B 18/1445 606/42 |
| 7,329,257 B2 | | 2/2008 | Kanehira et al. | |
| 7,766,910 B2 | | 8/2010 | Hixson et al. | |

(Continued)

FOREIGN PATENT DOCUMENTS

| CN | 101035482 A | 9/2007 |
| CN | 101522127 A | 9/2009 |

(Continued)

OTHER PUBLICATIONS

European Search Report for corresponding application EP13159631 dated Jun. 7, 2013.

(Continued)

*Primary Examiner* — Michael F Peffley
*Assistant Examiner* — Bo Ouyang
(74) *Attorney, Agent, or Firm* — Fitch, Even, Tabin & Flannery LLP

(57) ABSTRACT

In the case of an instrument (10) for coagulation and fusion as well as for severing vessels, provision is made for two shanks (19, 20), between which a vessel is to be gripped and fused. A blade (21) for severing the coagulated and fused vessel is provided with an isolator (40), which isolates the blade (21) against at least one of the electrodes or shanks (19, 20), respectively. On the other hand, the blade (21) is preferably in mechanical contact with at least one of the electrodes or shanks (19, 20), respectively, so that a safe (Continued)

separation of the fused biological tissue or vessel, respectively, is attained. This concept can be used to increase the safety of surgery and to miniaturize the tool (18) towards smaller sizes.

14 Claims, 4 Drawing Sheets

(56) References Cited

U.S. PATENT DOCUMENTS

| | | | | |
|---|---|---|---|---|
| 2003/0055424 | A1* | 3/2003 | Ciarrocca | A61B 18/1445 606/51 |
| 2005/0107785 | A1* | 5/2005 | Dycus | A61B 18/1445 606/51 |
| 2005/0159778 | A1* | 7/2005 | Heinrich | A61B 17/072 606/216 |
| 2006/0079879 | A1 | 4/2006 | Faller et al. | |
| 2009/0182327 | A1 | 7/2009 | Unger | |
| 2009/0218384 | A1 | 9/2009 | Aranyi | |
| 2010/0076433 | A1 | 3/2010 | Taylor et al. | |
| 2010/0312240 | A1* | 12/2010 | Boulnois | A61B 17/320016 606/48 |
| 2011/0087221 | A1 | 4/2011 | Siebrecht et al. | |
| 2011/0301607 | A1* | 12/2011 | Couture | A61B 18/1206 606/52 |
| 2012/0080338 | A1 | 4/2012 | Shelton, IV et al. | |
| 2013/0035687 | A1 | 2/2013 | Hiller et al. | |
| 2014/0155877 | A1 | 6/2014 | Yasunaga | |
| 2014/0194874 | A1* | 7/2014 | Dietz | A61B 18/1445 606/45 |

FOREIGN PATENT DOCUMENTS

| | | |
|---|---|---|
| CN | 102949236 A | 3/2013 |
| DE | 60226015 T2 | 6/2009 |
| EP | 1810625 A1 | 7/2007 |
| EP | 2554133 A1 | 2/2013 |
| JP | 2012139545 A | 7/2012 |
| JP | 201331663 A | 2/2013 |
| JP | 2013034568 A | 2/2013 |
| RU | 2006-113532 A | 11/2007 |
| SU | 980704 A | 12/1982 |
| WO | 9515124 A1 | 6/1995 |
| WO | 2008124271 A1 | 10/2008 |

OTHER PUBLICATIONS

Notice of Reasons for Rejection in corresponding Japanese application No. 2014-051504, dated Dec. 2, 2014, 7 pages.
Chinese office action in corresponding Chinese Application No. 201410094316.1, dated Sep. 25, 2015, 20 pages.
Japanese search report in corresponding Japanese Application No. 2014-051504, dated Dec. 1, 2014, 36 pages.
Korean office action in corresponding Korean Application No. 10-2014-0029675, dated Aug. 20, 2015, 4 pages.
Korean written opinion in corresponding Korean Application No. 10-2014-0029675, dated Oct. 19, 2015, 13 pages.
Chinese office action in corresponding Chinese Application No. 201410094316.1, dated May 23, 2016, 7 pages.
Russian Office Action in corresponding Russian Application No. 2014 109 850 dated May 7, 2018, with Machine English Translation (10 pages).
Russian Office Action and Search Report in corresponding Russian Application No. 2014 109 850 dated Dec. 18, 2017, with Machine English Translation (10 pages).

\* cited by examiner

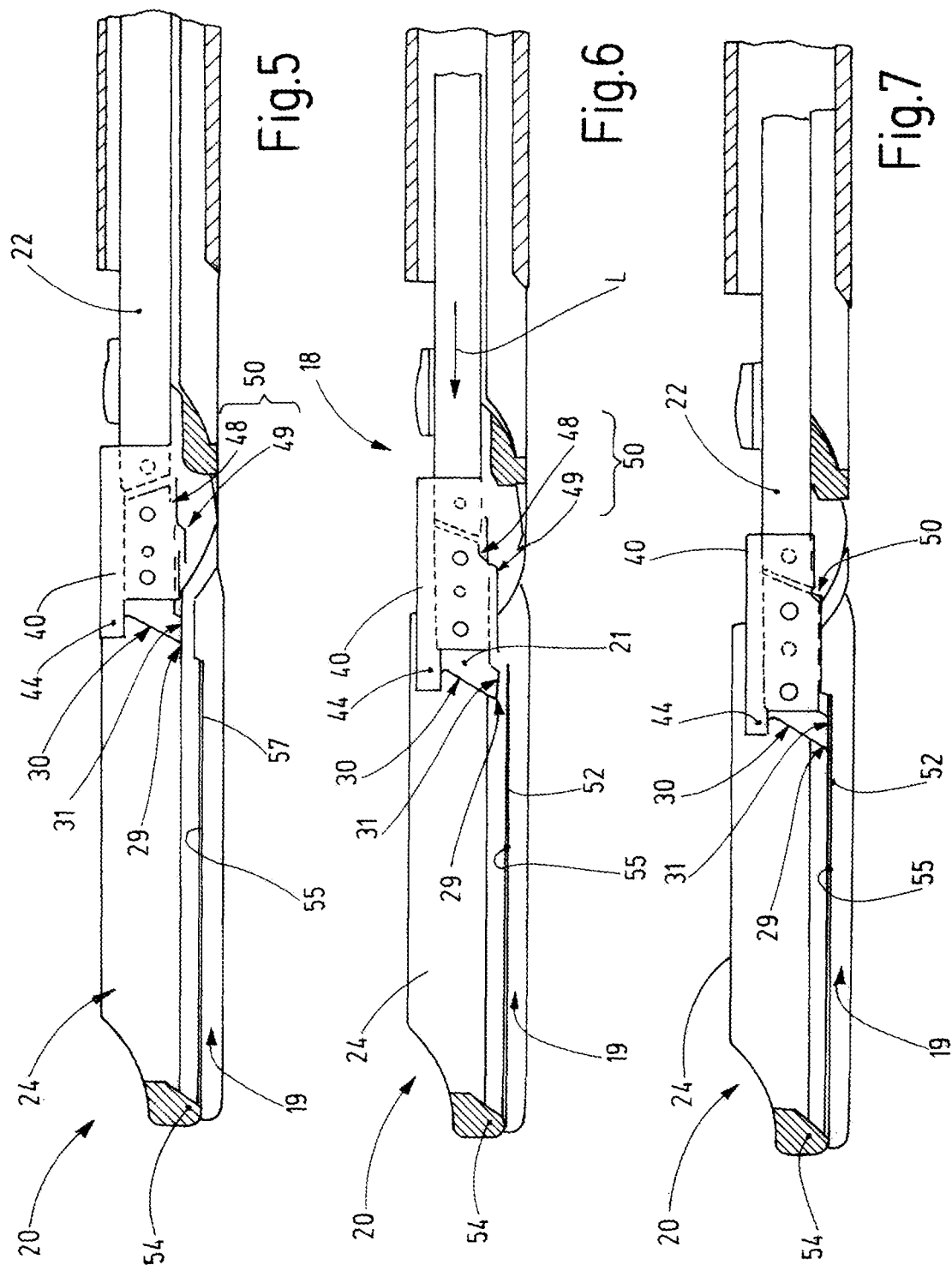

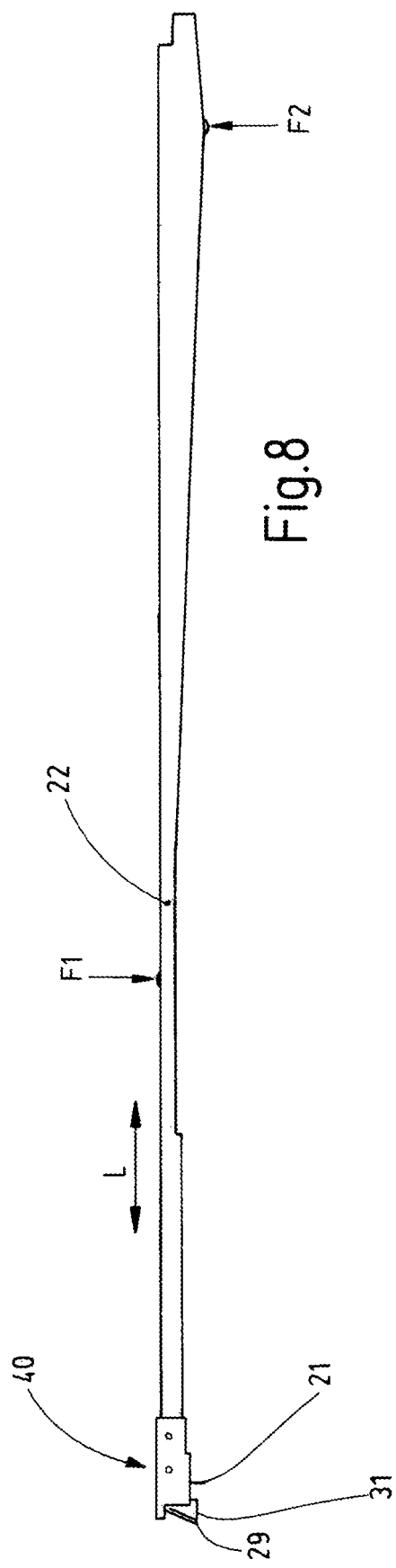

INSTRUMENT FOR VESSEL FUSION AND SEPARATION

RELATED APPLICATION(S)

This application claims the benefit of European Patent Application No. 13159361.8 filed Mar. 15, 2013, the contents of which are incorporated herein by reference as if fully rewritten herein.

TECHNICAL FIELD

The invention relates to an instrument for gripping, coagulating and severing tissue, in particular for clamping, closing and severing vessels, in particular blood vessels, on the living body of a human or animal patient.

BACKGROUND

Instruments for closing and separating blood vessels can be gathered from DE 602 26 015 T2, for example.

Typically, such instruments encompass an elongated shaft, which extends away from a handle. A tool comprising two shanks for clamping a blood vessel is arranged at the distal end of the shaft. In addition, a blade, which can be displaced longitudinally, is arranged at that location, so as to be able to sever a gripped and coagulated vessel. The shanks and the blade can be actuated via corresponding actuating elements on the handle. The shanks are embodied as electrodes and can be supplied with current systematically, so as to heat the vessel clamped therebetween and to fusion the vessel walls by means of coagulation.

Prior to the severing of blood vessels, it must be ensured that the coagulation took place took place to a sufficient extent, so that the ends of the severed vessel remain closed securely.

Based on this, it is the task of the invention to create an instrument for vessel fusion and separation, by means of which vessels can be closed and severed securely.

SUMMARY

One example instrument encompasses a tool comprising two shanks, at least one of is movable, so that they can be moved towards one another and away from one another. The two shanks form a jaw or a means for gripping tissue, respectively, which can be closed via a corresponding transfer element, for example a taut wire, which extends through the shaft. The tool further includes a blade, which, in the rest position, is located outside of a space defined between the shanks, and which can be inserted into this space by means of a drive element. The blade preferably consists of an electrically conductive material, for example stainless steel. The drive element can also be made of an electrically conductive material, for example stainless steel. To actuate the movable shank/shanks and the blade, one or a plurality of actuating elements, which serve the purpose of initially closing the jaw and to then retract the blade into the jaw, are attached to the housing. To connect the blade to the drive element, provision is made for an isolator, which provides a mechanical connection between the drive element and the blade, without permitting a current path between them. The embodiment of a parasitic current path, which could otherwise be created, in the event that the blade is possibly already moved slightly out of its rest position between the shanks during the coagulation process due to an operating error, is prevented thereby.

The measure according to one aspect of the invention thus also has the effect that the instrument can be used in different environments, for example also in accumulations of a physiological sodium chloride solution or similar electrically conductive fluids. The isolation of the blade from the drive element prevents or reduces, respectively, the possibility of parasitic current paths within the tool or shaft of the instrument and thus ensures that the current, which is to be applied to the biological tissue, actually moves through the biological tissue. The desired intensity of the coagulation process is ensured thereby. However, it is made possible in particular that the current supply of the shanks can be taken care of and/or continued, when the blade is moved from its rest position into the active position. It is avoided that the blade causes a short circuit between the shanks or its electrodes, respectively. It is prevented that electrical current passes by the tissue via the blade. The electrical current is guided from an electrode via the clamped tissue to the respective other electrode. The coagulation of the clamped tissue is thereby impacted in a positive manner and is ensured even in the event that the user actuates the blade prematurely. This is possible in particular in the case of two-stage tool drives, in the case of which an actuating handle is used to close the shanks while covering the first distance and to push the blade forward while covering a second, last distance. Should the situation arise that the user unknowingly moves the hand lever too far in the direction of the actuation position of the blade, the latter can already be moved slightly and can take over at least a part of the coagulation flow. The isolation of the blade according to the invention avoids this possible error.

The first electrode preferably encompasses a blade sliding surface, along which the blade can run. An electrical contact between the first electrode and the blade is created in this manner, at least during the severing of the coagulated vessel. A current flow, which can negatively influence the coagulation, can thus result between the coagulated tissue and the blade. The isolation of the blade avoids this current flow as well as damages to the blade or to its cutting edge or tip caused by current flow.

A vertical adjusting mechanism can be assigned to the blade, so as to adjust the blade as a function of its longitudinal movement at right angles, preferably vertically to this movement, so as to floatingly guide the tip of the blade and to only bring it in contact with the first electrode, but not with other edges, stages or the like. This protects the blade and ensures its lasting sharpness even in response to repeated use.

The two electrodes preferably encompass a shape, which is complementary to one another, so that, in the closed state, they define a gap of a substantially constant width between one another. This gap can be embodied so as to be flat or curved. The blade is arranged and guided such that it passes through this gap. Preferably, the blade thereby runs within one of the two shanks, which are embodied so as to be slit for this purpose, while it glides on the electrode of the other shank.

Preferably, the blade if embodied as a lamella, that is, as a thin metal plate. For example, it is made of a hardenable blade steel with a thickness of between 0.1 mm and 0.2 mm. It can encompass a length of several millimeters, for example between 7 mm and 10 mm, and a height of a few millimeters, for example between 2 mm and 3 mm.

At its distal end, it preferably encompasses a cutting nose comprising at least one cutting edge as well as a shaft, which extends away from the cutting nose. The cutting nose and the shaft can be embodied at the same metal piece and can thus merge seamlessly.

Preferably, the isolator is a plastic body, into which at least the shaft of the blade extends. The isolator thereby preferably covers at least the two flat lateral sides of the shaft and thus prevents extensive contact between the blade and biological tissue, which is present, as well as liquid, which might be present. In addition, the isolator extends above the shaft of the blade up to an isolator cutoff wall, which extends above the cutting nose. The isolator and its isolator cutoff wall (measured at right angles to the direction of movement of the blade) are thicker than the blade, in particular thicker than its cutting nose. Every electrical contact between the blade and the second shank, in the slit of which the blade can be retracted, is thus avoided. The cutting nose is arranged so as to be protected in a recess of the isolator.

It is advantageous, when the shaft as well as the drive element in each case encompass at least one opening, which is permeated by the isolator. In this manner, a form lock is obtained between the isolator and the drive element as well as between the isolator and the blade. More preferably, the blade and the drive element determine a gap, which can be embodied as parallel gap. This gap can be filled with material of the isolator. Preferably, this gap is oriented transversely to the direction of movement of the blade. This results in a mechanically durable connection between the drive element and the blade, via which the drive element is not only capable of transferring traction and pressure, but also a pressing force, which is directed vertically thereto, to the blade. This pressing force can press the blade against the non-slitted first electrode and can thereby support a clean severing of the coagulated tissue.

Further details of advantageous embodiments of the invention are the subject matter of the drawing, of the description or of subclaims. Direction-related terms, such as top, bottom, upper, lower, etc., which are used in the description of an exemplary embodiment, refer to directions in the drawing and should not be interpreted to be limiting in this respect.

BRIEF DESCRIPTION OF THE DRAWINGS

FIGS. 5 to 7 show the tool comprising closed shanks in different actuating positions and FIG. 8 shows the blade, the drive element and the isolator according to FIG. 4 in general view.

DETAILED DESCRIPTION

Figure 1:
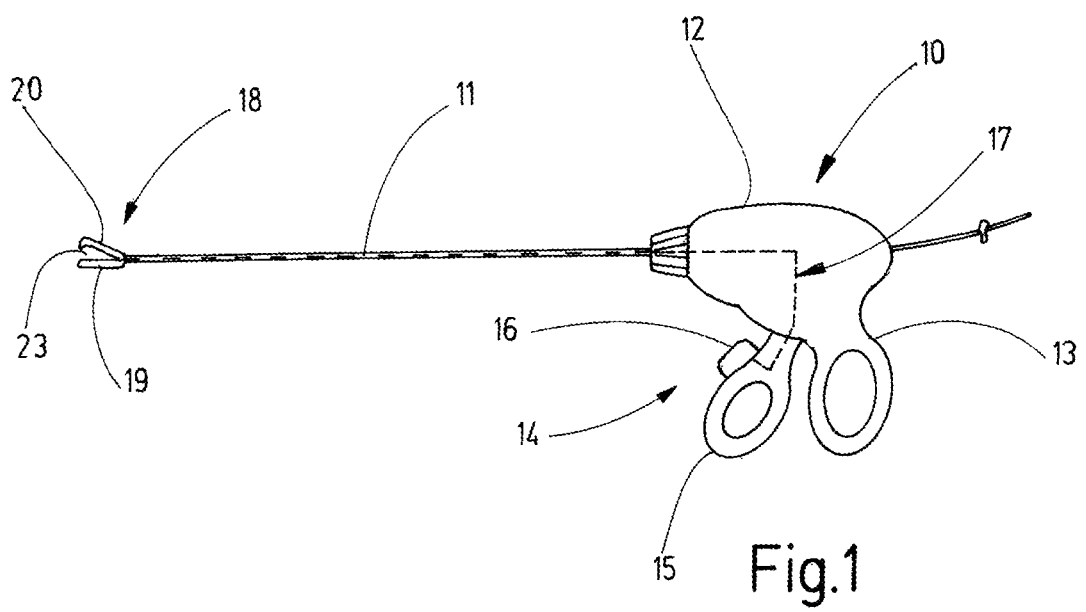
FIG. 1 shows an instrument according to the invention in a schematic representation.

FIG. 1 illustrates an instrument 10, which can serve to clamp, fusion and sever biological tissue, for example a vessel, e.g., of a blood vessel when operating on a human or animal body. The instrument 10 can be used in particular for endoscopic surgery. It encompasses a slim shaft 11, which is held on a housing 12 at its proximal end. Said housing encompasses a handling means, such as, for example, a handle 13, as well as actuating elements 14. The latter can consist, for example, of a pivotable gripping member 15 and/or of an actuating button or lever 16 as well as of further elements, if applicable, e.g. electrical switches. The actuating elements 14 are connected to a tool 18, which is arranged at the distal end of the shaft 11, via power transmission means 17, which are only illustrated schematically in FIG. 1 in a dashed manner. The tool 18 comprises at least two shanks 19, 20, as well as a blade 21. The shanks 19, 20 serve to clamp tissue, for example of a vessel, in that they are moved towards one another, wedge the vessel between one another and coagulate it. The blade 21 serves the purpose of severing the coagulated vessel.

The power transmission means can include thrust or traction members for moving one or both shanks 19, 20, as well as a drive element 22 for actuating the blade 21. Such a drive element 22 can be, for example, a metal strip 22, which consists of a thin sheet, as it can be seen from FIG. 8. The drive element 22 extends from the blade 21 through a partial area of the shaft 11 up to the traction and thrust members. The latter, in turn, extend to a drive, which is not illustrated in detail, which transfers a drive movement, which starts at the gripping member 15, to the blade 21.

Figure 2:
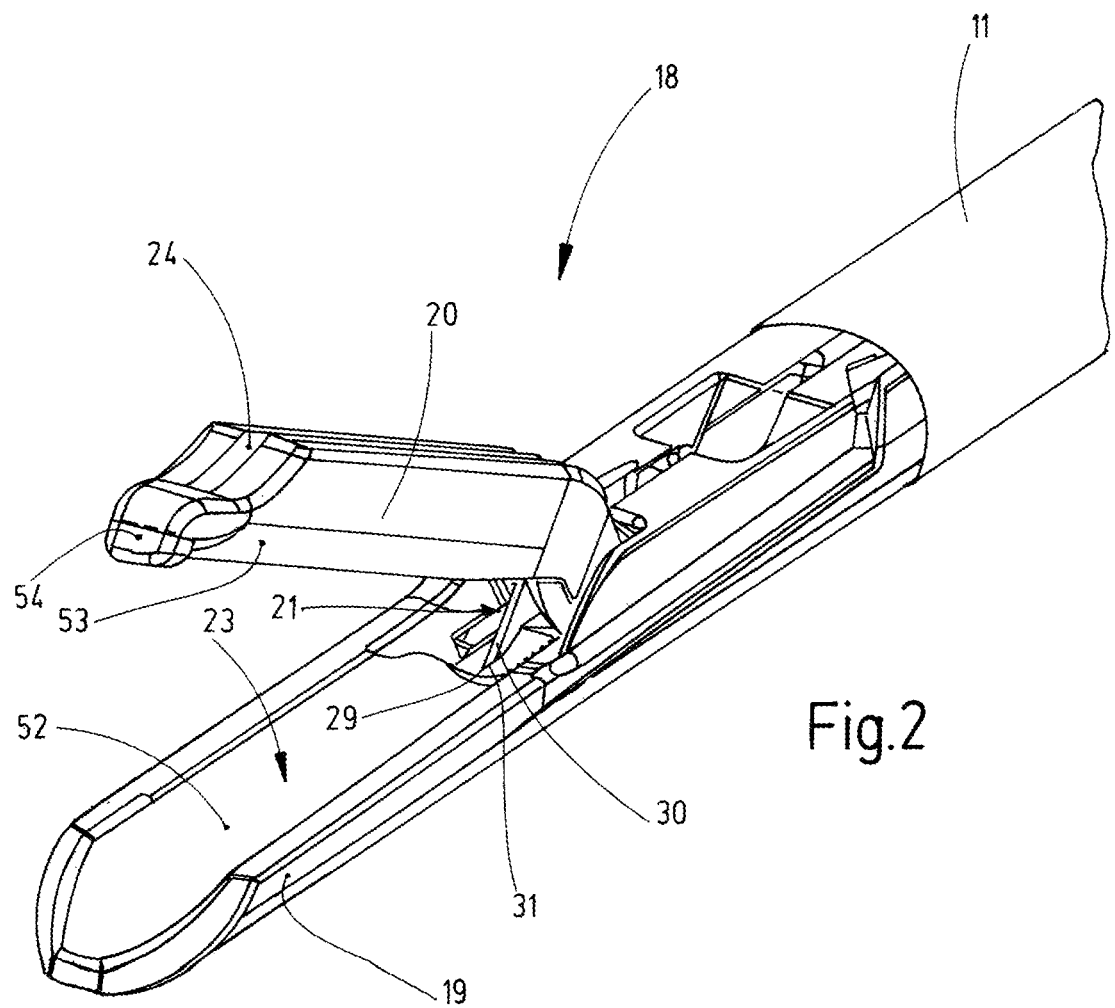
FIG. 2 shows the tool of the instrument according to the invention, in perspective view.

For example, the drive can be embodied such that the shanks 19, 20 are initially closed in response to the movement of the gripping member 15 towards the handle 13, wherein the blade 21 still remains in rest position, that is, outside of a space 23, which is enclosed between the shanks 19, 20. This state is illustrated in FIG. 2. The drive can further be embodied such that the blade 21 is pushed forward towards the distal end of the tool 18 between the shanks 19, 20 during the last part of the movement of the gripping member 15 towards the handle 13 when the shanks are already closed. For this purpose, one of the shanks 19, 20, for example the shank 20, can be provided with a slit 24, which extends longitudinally through the shank 20, so as to accommodate the blade 21. The slit 24 can furthermore be seen from FIG. 3. Instead of the above-described drive, which derives the movement of the shanks 19, 20 and of the blade 21 from a movement of an actuating member (e.g. gripping member 15), provision can also be made for other actuating members, in particular separate actuating members, for the tool 18 and for the blade 21.

Figure 3:
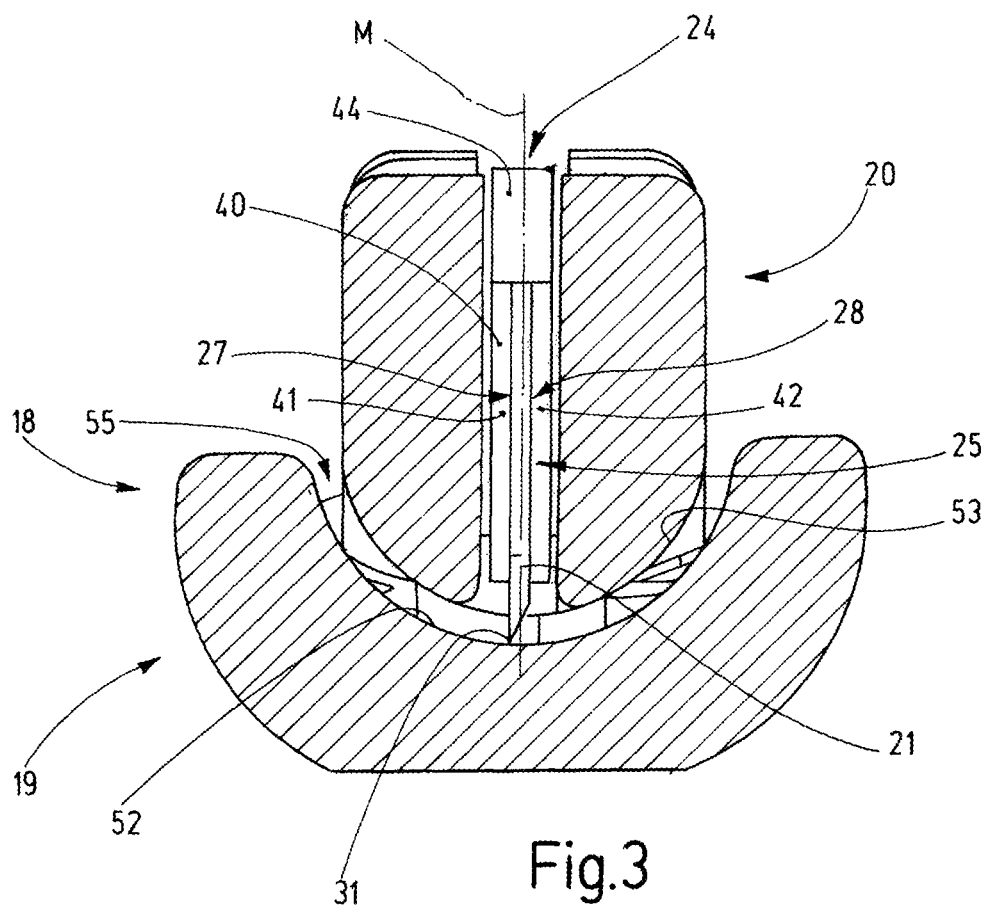
FIG. 3 shows the tool according to FIG. 2, in cross section.
Figure 4:
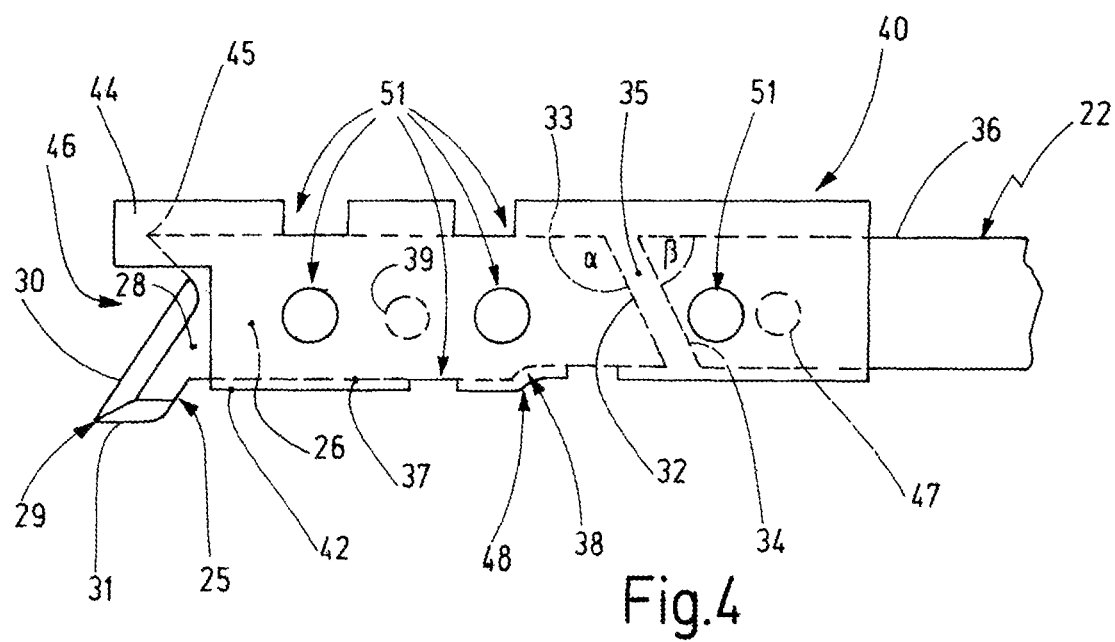
FIG. 4 shows a blade, isolator and drive element of the tool according to FIG. 3, in a partial side view.

The blade 21, which is guided in the slit 24, consists of a metal lamella, for example, which, as can be seen from FIG. 4, encompasses a cutting nose 25 at its distal end, and a shaft 26, which connects thereto. The cutting nose 25 and the shaft 26 are preferably a part of a small metal plate with a thickness of between 0.1 mm and 0.2 mm, preferably 0.15 mm, comprising two flat sides 27, 28, which can be seen from FIG. 3. The cutting nose 25 forms a blade comprising a tip 29, from which a front cutting edge 30 extends away so as to ascend transversely. At an acute angle thereto and thus parallel to the first shank 19, the cutting nose 25 encompasses a cutting edge 31, which glides along the first shank 19 when in use.

The shaft 26, which has a rectangular cross section, extends away from the cutting nose 25 and ends at an edge 32, which is preferably staged or which is also arranged transversely, as illustrated. Said edge preferably draws an obtuse angle α of, for example, between 110° and 130°, for example 115°, with the upper edge 33 of the shaft 26, which is preferably straight.

Located opposite the edge 32, the drive element 22 encompasses a frontal edge 34, which is preferably oriented parallel to the edge 32 and which thus defines a parallel gap 35 therewith. The edge 34 preferably draws an acute angle β of 65°, for example, with the upper side 36 of the drive element 22.

The lower edge 37, which extends approximately parallel to the upper side 33 of the shaft 26, is preferably embodied so as to be straight and can be provided with a stage 38. In addition, the shaft 26 preferably encompasses at least one opening 39. The latter can be embodied so as to be round, angular or otherwise. It serves to secure an insulator 40, which is preferably formed by a plastic part in a form-locking manner. The isolator 40 envelopes the shaft 26 of the blade 21 at least partially, wherein the isolator 40 preferably leaves open the cutting nose 25 of the blade 21. The isolator 40 can be formed by a plastic injection molding part, preferably consisting of a temperature-resistant thermoset material. As can be seen from FIG. 3 in combination with FIG. 4, the isolator preferably encompasses two flat sections 41, 42, which cover the sides 27, 28 of the shaft 26 and which are connected among one another by means of a section, which extends through the opening 39. The sections 41, 42 can be connected among one another above the upper side of the shaft 26 as well as below the lower edge 37, so that a compact isolation body is formed as a whole. As is shown in FIG. 4, the common lower closure of the sections 41, 42 runs below the lower edge of the shaft 26, but above the cutting edge 31.

As is shown in FIG. 4, the drive element 22 extends into the isolator 40 and is enclosed by it. At its distal end, the isolator 40 preferably encompasses an isolator cutoff wall 44, which encloses a leading end 45 of the blade 21 and which extends beyond the cutting nose 25. A free space 46, which forms an inset corner, preferably comprising a right angle, is embodied below the isolator cutoff wall. The cutting nose 25 is arranged in the free space 46. According to FIG. 3, the isolator cutoff wall 44 is thicker than the cutting nose 25, which can thus not touch the inner wall surfaces of the slit 24.

Provision can be made in the drive element 22 for an opening 47, which is permeated by material of the isolator 40, so as to connect the drive element 22 and the isolator 40 in a form-locking manner. The material of the isolator 40 can furthermore fill the parallel gap 35.

As is shown in FIG. 3, the isolator 40 is preferably embodied so as to be flat on its two sides. The sections 41, 42 encompass a thickness of between 0.1 mm and 0.3 mm. In the area of the shaft 26, the material thickness of the sections 41, 42, is between 0.2 mm and 0.3 mm, e.g., preferably 0.26 mm. In the area of the drive element 22, the material thickness of the corresponding sections of the isolator 40 is preferably between 0.1 mm and 0.2 mm, e.g. 0.16 mm. A sufficient mechanical stability as well as a desired electrical isolation in particular of the cutting nose 25 is thus obtained due to a sufficient gap to the sides of the slit 24.

At the stage 38, the isolator 40 can also be provided with a stage 48 on its lower side. Said stage 48, together with a stage 49, which is provided at the first shank 19 or the shaft 11, forms a vertical adjusting mechanism 50 (see FIGS. 5 to 7). As is shown in FIG. 4, provision can additionally be made at several locations of the isolator 40 for recesses 51, by means of which the shaft 26 or a free end of the drive element 22 can be accessed. These recesses 51 can serve to position the blade 21 and the drive element 22 during the production of the isolator 40 by means of master forming.

Starting at the isolator 40, the drive element 22 extends through the entire shaft 11 and thereby serves to move the blade 21 in longitudinal direction L. For this purpose, the drive element 22 is embodied so as to be traction and compression-resistant. In addition, it runs in the shaft 11 along corresponding opposite surfaces, which, as is illustrated in FIG. 8 by means of arrows, exert position-dependent forces F1 and F2 on the drive element 22. These forces are transferred to the blade 21 by means of the isolator 40, so that the tip 29 and cutting edge 31 thereof glide along the first (lower) shank 19 at a pretension.

The instrument 10, which has been described in this respect, operates as follows:

In the position, which is illustrated in FIGS. 1 and 2, the instrument 10 is led to a vessel such that the latter is located between the two shanks 19, 20. The user then pulls the gripping member 15 towards the handle 13, whereby the shanks 19, 20 are initially closed when the blade 21 is still in the retracted position. The vessel is thus gripped between the electrode surface 52 of the first shanks 19 and the electrode surface 53 of the second shank 20 and is squeezed to the extent that the vessel walls, which are located opposite one another, touch. The user can now initiate the activation of the electrode surfaces 52, 53 via the actuation button 16, wherein a current, which serves for coagulating the vessel, is guided to the shanks 19, 20. For example, this can be a high-frequency AC voltage. A nose, which is provided at the distal end of one of the shanks, for example the shank 20, or another projection 54 thereby ensures that a defined gap 55 is maintained between the shanks 19, 20. The current flow between the electrode surfaces 52, 53 runs completely via the biological material, which is gripped therebetween and coagulates it. As is shown in FIG. 5, the blade 21 is thereby in the retracted position.

In the event that the user now wants to sever the coagulated vessel, he moves the gripping member 15, if necessary by overcoming an increased resistance, further against the handle 13, whereupon the blade 21, as can be seen from FIG. 6, is inserted into the slit 24 of the shank 20. The vertical adjusting mechanism 50 thereby holds the tip 29 and the edge 31 so as to still float above the electrode surface 52 of the shank 19. In the further course of the forwards movement, the cutting edges 31 and the tip 29, however, lower onto the electrode surface 52, as is illustrated in FIGS. 6 and 7. The drive element 22 now pushes the blade 21 forward up to the projection 54 and severs the coagulated vessel. The isolator 40 thereby interrupts every current path between the blade 21 and the second electrode surface 52 as well as the shank 20 and thus ensures that the blade 21 does not take over any noteworthy portion of the current, which serves for the coagulation, even if it reaches the slit slightly prematurely. Finally, this even makes it possible to sever vessels during the final phase of the coagulation of the vessel ends, which are clamped between the shanks 19, 29. A shortening of surgery time can be attained with this. However, is it essential that an increase of the coagulation reliability occurs. Even if the blade 21 is actuated prematurely, this does not influence the quality of the coagulation result.

It is important to point out that the isolator 40 can also include the entire drive element 22. In this case, the blade 21 and the drive element 22 can be embodied in one piece or can be connected to one another otherwise.

In addition, it is important to point out that the drive element can also be made of an electrically non-conductive material, either completely or partially. In this case, the isolator 40 can be a part of the drive element 22. E.g., the distal end of the drive element 22 can form the isolator 40.

In the case of an instrument 10 for coagulation and fusion as well as for severing vessels, provision is made for two shanks 19, 20, between which a vessel is to be gripped and fused. A blade 21 for severing the coagulated and fused vessel is provided with an isolator 40, which isolates the blade 21 against at least one of the electrodes or shanks 19, 20, respectively. On the other hand, the blade 21 is preferably in mechanical contact with at least one of the electrodes or shanks 19, 20 such that a safe severing of the fused biological tissue or vessel, respectively, is attained. This concept can be used to increase the safety of surgery and to miniaturize the tool 18 towards smaller sizes.

LIST OF REFERENCE NUMERALS 10 instrument
11 shaft
12 housing
13 handle
14 actuating elements
15 gripping member
16 actuating button or lever
17 power transmission means
18 tool
19 first shank
20 second (upper) shank
21 blade
22 drive element for 21
23 space between the shanks 19 and 20
24 slit in 20
25 cutting nose of 21
26 shaft
27, 28 flat sides of 26
α, β angle
29 tip of 25
30 front cutting edge of 25
31 cutting edge at lower side of 25
32 rear side edge of 26
33 upper side of 26
34 frontal edge of 22
35 parallel gap
36 upper side of 22
37 lower edge of 26
38 stage of the lower edge of 26
39 opening in 26
40 isolator
41, 42 sections
44 isolator cutoff wall
45 distal end of the blade 21
46 free space
47 opening in 22
48 stage at 40
49 stage at 19
50 vertical adjusting mechanism
51 positioning recesses in 40
52 electrode surface of 19
53 electrode surface of 20
54 projection
55 gap between the shanks 19 and 20
L longitudinal direction

What is claimed is:

1. An instrument (10) for vessel fusion and separation, the instrument comprising:
    a longitudinal shaft (11), which extends away from a housing (12) and which supports a tool (18) at its distal end, wherein the tool comprises:
    a first shank (19) having a first electrode surface (52),
    a second shank (20), which is supported so as to be movable towards the first electrode surface (52) and away from it, wherein the second shank (20) has an electrode surface (53) and a longitudinal slit (24),
    a blade (21) comprising a cutting portion and a blade shaft (26) and having an electrically conductive material, wherein the blade is arranged so as to be movable in a direction relative to the shaft (11) and so as to extend into the longitudinal slit (24) or so as to be retractable into it;
    a drive element (22), which extends from the housing (12) through the shaft (11) to the blade (21); and
    an electrical isolator (40), which is arranged so as to connect the blade (21) and the drive element (22) to one another and to electrically isolate the blade (21) and the drive element (22) from each other;
    wherein the electrical isolator extends along either side of the blade to electrically isolate the blade from the second shank, wherein the electrical isolator is sized and configured to guide the blade within the longitudinal slit of the second shank;
    wherein the blade shaft (26) extends into the electrical isolator (40);
    wherein the blade (21) including the blade's shaft and the drive element (22) define a gap (35) between one another such that blade and drive element are electrically isolated from one another and are interconnected solely by the electrical isolator; and
    wherein the blade shaft (26) encompasses at least one opening (39), which is permeated by the isolator (40), and the drive element (22) encompasses at least one opening (47), which is permeated by the isolator (40).

2. The instrument according to claim 1, wherein the first electrode surface (52) is a blade gliding surface.

3. The instrument according to claim 1, wherein a vertical adjusting mechanism (50) connected to adjust the blade (21) at right angles to the longitudinal movement as a function of its longitudinal movement, wherein the vertical adjusting mechanism (50) is equipped to move the blade (21) vertically towards the first electrode surface (52) in response to a forwards movement, which is oriented along the first shank (19), and to move it vertically away from the first electrode surface (52) in response to a retraction movement, which is oriented along the first shank (19).

4. The instrument according to claim 1 wherein the second shank (20) is formed by a metal body, wherein a side of the metal body facing the first electrode surface (52) of the first shank (19) defines a shape following a shape of the first electrode surface (52).

5. The instrument according to claim 1, wherein at least one of the shanks (19, 20) comprises a projection (54), so as to fix a gap (55) between the first electrode surface (52) and the second electrode surface (53) of the second shank (20) when the shanks (19, 20) of the instrument (10) are closed.

6. The instrument according to claim 1, wherein the drive element (22) is electrically conductive.

7. The instrument according to claim 1, wherein the blade (21) is embodied as a lamella comprising two flat lateral sides (27, 28).

8. The instrument according to claim 1, wherein the cutting portion of the blade (21) comprises a cutting nose (25).

9. The instrument according to claim 8, wherein the cutting nose (25) comprises:
    a sharpened cutting edge (31), which faces the first electrode surface (52) and which is arranged parallel thereto, and
    a cutting edge (30), which is sharpened on the front side and which is oriented at an angle to the direction of the movement of the blade (21).

10. The instrument according to claim 1, wherein the isolator (40) encompasses an isolator cutoff wall (44), which is arranged above a cutting nose (25) of the blade (21).

11. The instrument according to claim 1, wherein the drive element (22) extends into the isolator (40).

12. The instrument according to claim 1, wherein the gap (35) is oriented transversely to the direction of movement of the blade (21).

13. A method of operation of an instrument for vessel fusion and separation, the instrument comprising a first shank having a first electrode surface, a second shank having a second electrode surface and defining a longitudinal slit, a blade having an electrically conductive material and disposed to be movable in a shaft, a drive element, and an electrical isolator connecting the blade and the drive element to each other, the method comprising:
- closing the first shank and the second shank together to trap a vessel between the first electrode surface and the second electrode surface to cause vessel walls of the vessel to touch;
- coagulating the vessel by application of current through the first electrode surface and the second electrode surface;
- blocking flow of the current to the blade, the first shank, and the second shank with the isolator, which isolates the blade by surrounding a portion of the shaft of the blade, wherein the blade including the blade's shaft and the drive element define a gap between one another such that blade and drive element are electrically isolated from one another and are interconnected solely by the electrical isolator and wherein the blade shaft encompasses at least one opening, which is permeated by the isolator, and the drive element encompasses at least one opening, which is permeated by the isolator, wherein the electrical isolator extends along either side of the blade to electrically isolate the blade from the second shank, wherein the electrical isolator is sized and configured to guide the blade within the longitudinal slit of the second shank;
- driving the blade in a forward direction through the longitudinal slit to sever the vessel.

14. The method of claim 13 further comprising adjusting the blade in a direction approximately perpendicular to longitudinal movement of the blade along including moving the blade into contact with the first electrode surface in response to the forward movement of the blade.

* * * * *